United States Patent
Bess et al.

(10) Patent No.: US 6,359,011 B1
(45) Date of Patent: Mar. 19, 2002

(54) DENATURANTS FOR SYMPATHOMIMETIC AMINE SALTS

(75) Inventors: William Stefan Bess, Edison; William Michael Nichols, Fanwood, both of NJ (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 09/391,739

(22) Filed: Sep. 8, 1999

Related U.S. Application Data

(60) Provisional application No. 60/099,712, filed on Sep. 10, 1998.

(51) Int. Cl.[7] ............................................. A61K 31/135
(52) U.S. Cl. ........................................ 514/646; 424/166
(58) Field of Search ............................ 424/166; 514/646

(56) References Cited

U.S. PATENT DOCUMENTS

| | | | |
|---|---|---|---|
| 3,169,092 A | 2/1965 | Petraglia et al. | 167/65 |
| 3,773,920 A | * 11/1973 | Nakamoto et al. | 424/19 |
| 4,265,875 A | 5/1981 | Byrne et al. | 424/19 |
| 4,493,827 A | 1/1985 | Valle | 424/166 |
| 4,601,894 A | * 7/1986 | Hanna et al. | 424/19 |
| 4,657,757 A | 4/1987 | Hanna et al. | 424/488 |
| 5,407,686 A | 4/1995 | Patel et al. | 424/468 |

FOREIGN PATENT DOCUMENTS

| | | |
|---|---|---|
| EP | 0294103 | 12/1988 |
| EP | 0523847 | 1/1993 |
| EP | 0717986 | 6/1996 |
| SU | 1146046 | 3/1985 |
| WO | WO 9428870 | 12/1994 |
| WO | WO 9511034 | 4/1995 |
| WO | WO 95/11034 A1 * | 4/1995 |
| WO | WO 9608252 | 3/1996 |
| WO | WO 9621431 | 7/1996 |
| WO | WO 9737689 | 10/1997 |
| WO | WO 97/37689 A2 * | 10/1997 |
| ZA | 9004021 | 2/1991 |

OTHER PUBLICATIONS

Lehmann, Klaus O.R. et al.; Controlled drug release from small particles encapsulated with acrylic resins; Midl. Macromol. Monogr. (1978), 5 (Polym. Delivery Syst.), pp. 111–119.

Aloamaka et al. Effect of Pregnancy on Relaxation of Rat Aorta to Magnesium; Cardiovascular Research; 1993, vol. 27, No. 9, pp. 1629–1633.

Uncle Fester; Secrets of Methamphetamine Manufacture Fourth Edition; 1996; pp. 154–159.

* cited by examiner

*Primary Examiner*—Dwayne C. Jones
(74) *Attorney, Agent, or Firm*—Barry H. Jacobsen

(57) ABSTRACT

The instant invention makes impractical the use of sympathomimetic amine compositions in illicit drug production. More specifically, the preparation of methamphetamine from the disclosed pseudoephedrine hydrochloride formulations is inhibited. The present invention defines pharmaceutical compositions comprising a sympathomimetic amine salt and at least one combination inhibitor, the combination inhibitor which acts both to interfere with the isolation of the sympathomimetic amine from the composition and to interfere with the conversion of the sympathomimetic amine to another pharmacologically active compound. The contemplated compositions may also include reaction and separation inhibitors in any mixture to assure maximum protection against the use of the sympathomimetic amine-containing compositions for illegal drug manufacture. The presence of the combination, reaction and separation inhibitors does not significantly alter the release of the sympathomimetic amine from the composition.

29 Claims, No Drawings

DENATURANTS FOR SYMPATHOMIMETIC AMINE SALTS

This application claims priority to U.S. provisional application No. 60/099,712, filed Sep. 10, 1998.

BACKGROUND OF THE INVENTION

Field of the Invention

The present invention relates to pharmaceutical compositions comprising a sympathomimetic amine salt and at least one combination inhibitor, the combination inhibitor which acts both to interfere with the isolation of the sympathomimetic amine from the composition and to interfere with the conversion of the sympathomimetic amine to another pharmacologically active compound.

Sympathomimetic Amines and the Problem of Unconventional Use

The acid salts of sympathomimetic amines are widely used active agents in over-the-counter (OTC) pharmaceuticals. As their name suggests, this class of compounds produces pharmacological effects which mimic the activation of the sympathetic nervous system. For example, the hydrochloride salt of the sympathomimetic amine pseudoephedrine is a commonly used active ingredient in OTC decongestant products. It acts by causing adrenergic nerve endings to release norepinephrine, thereby stimulating alpha and beta norepinephrine receptors, particularly of the upper respiratory tract. This, in turn, results in vasoconstriction and shrinkage of swollen tissues in the sinuses and nasal passages. Its wide usage in numerous OTC products makes it readily available and easily accessible to the general public. When used in a recommended manner for approved indications, OTC pseudoephedrine hydrochloride pharmaceuticals are safe and effective. However, a problem arises when pseudoephedrine hydrochloride-containing OTC pharmaceuticals are used in an unconventional manner. Specifically, this active ingredient from OTC products is also a convenient starting material in the production of the pharmacologically active agent methamphetamine.

Methamphetamine is a powerful stimulant of the central nervous system (CNS). One of its principle pharmacological effects is the release of high levels of the neurotransmitter dopamine which stimulates brain cells. The approved therapeutic uses for methamphetamine are very limited, and such approved uses are commonly associated with the treatment of obesity. However, methamphetamine's pharmacological effects make it a popular candidate for illegal use as a recreational drug rather than as a legitimate therapeutic agent. Methamphetamine has various street names which include "speed", "meth" and "crank". In its hydrochloride salt form it appears as crystals and is referred to as "ice", "crystal" and "glass". When taken intravenously or by smoking, methamphetamine causes a burst of intense sensation which has been described as highly pleasurable. Oral or intranasal use causes a less intense euphoric high. Methamphetamine addiction can occur quickly and is characterized by increasing frequency and dosage of the drug. The CNS effects of the drug include irritability, insomnia, confusion, tremors, hyperthermia, convulsions, anxiety, paranoia and aggressiveness. In more extreme cases methamphetamine causes heart rate and blood pressure changes which can ultimately contribute to cardiovascular collapse and death.

As a natural progression, the illegal use of methamphetamine results in a demand for access to the drug through illicit routes. These illicit routes, in turn, are often supplied by the illegal production of the compound. One of the main methods used in the illegal synthesis of methamphetamine is known as the ephedrine reduction method. This procedure is relatively simple, requiring only a few steps and a small number of reagents to carry out the chemical process. The starting material used in this method is either ephedrine or pseudoephedrine. Previously, ephedrine, an enantiomer of pseudoephedrine, was the starting material of choice in the production of illegal methamphetamine. However, since regulatory efforts in the United States have significantly reduced the ease by which ephedrine can be obtained, pseudoephedrine or its corresponding salts from OTC products have become the preferred starting point for the production of illicit methamphetamine. The wide public availability of pseudoephedrine hydrochloride in OTC pharmaceuticals allows illicit drug manufacturers easy and abundant access to a suitable starting material for clandestine methamphetamine chemistry.

Methamphetamine abuse in the United States is expanding geographically as well as in numbers among the younger population. Traditionally the illegal use of this compound was predominantly localized in the west and southwest United States. However, trafficking patterns now have been detected in areas of the country previously not known to have problems with the illicit use of this drug, namely the midwest. Furthermore, among young adults the illegal use of methamphetamine is increasing. For example, in 1997 4.4% of high school seniors had used crystal methamphetamine at least once in their lifetime—up from 2.7% in 1990.

The increasing and broadening scope of illegal use of methamphetamine, combined with the decreased availability of ephedrine as a synthetic starting material for methamphetamine production, indicates the demand for OTC preparations of pseudoephedrine hydrochloride by illicit drug manufacturers will continue to escalate. The unconventional use of OTC pseudoephedrine can be combated by limiting the accessibility of such preparations to the general public. However, this restriction adversely impacts the consumer who seeks to use properly these safe and effective drugs and who has come to rely on ready access to them without the continuous authorization of a health care professional (e.g., physicians or pharmacists). The goal of the instant invention is to significantly deter the use of OTC products in illicit drug preparations without compromising the accessibility of these products to the general public.

Prior Attempts to Minimize Illicit Use of OTC Pharmaceuticals

Attempts to use the active ingredients in OTC pharmaceutical products to prepare illegal drugs is not uncommon. In response, various efforts have been made to modify pharmaceutical preparations in order to prevent this type of illicit use of these products. For example, codeine can be extracted from analgesic tablets and converted to morphine and heroin. Application WO 96/08252 disclosed codeine-containing solid dosage forms comprising components that interfere with the isolation of the active ingredient.

In the case of compositions containing sympathomimetic amines, WO 97/37689 which corresponds to U.S. Ser. No. 08/937,408 filed on Apr. 1, 1997, discloses modified pharmaceutical preparations which comprise denaturing components that complicate the use of these formulations in the illegal synthesis of drugs. The main mechanism by which such a denaturant system is effective involves creating an infeasible physical separation of the sympathomimetic amine from the formulation; this denaturant system is designed to combat widely known and used methods of preparing illegal drugs from OTC products. Comparatively, the sympathomimetic amine pharmaceutical composition of the instant invention offers the unique advantage in that it comprises a combination inhibitor which is a single component that remains with the amine when the composition is subjected to attempted separation. Such a component is not only effective against well known extraction methods commonly employed by illegal drug manufacturers, but it also deters alternate, and possibly more sophisticated means of sympathomimetic amine isolations.

The combination inhibitors in the instant invention offer a second, critical advantage over previously described denaturant systems used to inhibit methamphetamine synthesis from OTC pseudoephedrine preparations; in addition to hindering the isolation of the sympathomimetic amine, these combination inhibitors also chemically interfere with the conversion of the amine to other pharmacologically active compounds. This reaction interference occurs either when the chemical conversion is carried out on the original formulation or on a composition that has undergone an extraction; interference is effective on an extracted composition since at least a portion of the combination inhibitor remains with the sympathomimetic amine under a broad range of extraction conditions. Theoretically, a combination inhibitor chemically reacts in multiple ways to prevent the conversion of the sympathomimetic amine to another compound. A combination inhibitor may react not only with itself and other reagents directed to the sympathomimetic amine, but it also may react with the amine. Since the combination inhibitor reacts with the principle starting material such as pseudoephedrine, addition of increased amounts of reactants will not likely overcome to any significant extent the reaction of the inhibitor with the sympathomimetic amine. Furthermore, the generation of multiple side products requires sophisticated separation techniques to isolate any minimal amount of methamphetamine that may be generated.

The present invention addresses the problem of the use of widely available OTC sympathomimetic amine formulations in the preparation of illegal drugs by disclosing novel pharmaceutical compositions that are impractical as starting material in illegal drug synthesis. These compositions are effective in deterring both well known extraction methods as well as different and possibly more sophisticated illegal drug production methods. Furthermore, the compositions of the present invention are not compromised in their release, bioavailability or dosing frequency relative to corresponding, undenatured sympathomimetic amine preparations presently available to the consumer.

SUMMARY OF THE INVENTION

The incorporation of at least one combination inhibitor in pharmaceutical compositions of sympathomimetic amines, the subject of this invention, represents a unique discovery in the area of drug formulations involving this class of active agents. The purpose of the combination inhibitor is to prevent the use of OTC sympathomimetic amine pharmaceuticals in the production of illegal drugs, particularly the synthesis of methamphetamine from pseudoephedrine. It achieves this purpose by interfering with both the isolation of the sympathomimetic amine from the composition and the conversion of the sympathomimetic amine to other pharmacologically active compounds. The combination inhibitor is present in an amount sufficient to accomplish the goal without significantly altering the release, bioavailability or dosage of the active ingredient. The advantage of the present invention is that a single component deters both traditional extraction conditions used in illegal drug synthesis as well as alternate, more sophisticated separation techniques.

DETAILED DESCRIPTION OF THE INVENTION

General Terms and Definitions

The term "inhibitor" as used in the instant invention is any component, added to a composition containing a sympathomimetic amine, that interferes with the isolation of that sympathomimetic amine and/or interferes with the conversion of that sympathomimetic amine to another pharmacologically active compound. A single inhibitor of any class (i.e., combination, reaction or separation) or any mixture of more than one inhibitor of the same or of multiple classes of inhibitors will not significantly effect the release of the sympathomimetic amine from the formulation as compared to the undenatured composition. The term inhibitor is interchangeable with the term "denaturant". A "pharmacologically active compound" is any chemical substance that affects living tissue, producing a biological effect in a living organism.

The terms "immediate release" and "modified release" are used in the instant invention as they are commonly understood in the pharmaceutical industry. For immediate release products in solid dosage form (such solid dosage forms including but not limited to tablets, capsules, powders and films), release is defined as the amount of sympathomimetic amine measured using an appropriate USP dissolution test procedure with distilled water as the medium. If no official USP dissolution test procedure has been established, (e.g., as in the case of chewable tablets), then the most appropriate USP dissolution test will apply, utilizing distilled water as the medium and taking measurements at appropriate time points up to and including the final dosing interval. For immediate release products in non-solid dosage form (such non-solid dosage forms including but not limited to liquids, syrups, elixers, liquid center oral products, creams, pastes and gels), release is defined as the amount of sympathomimetic amine measured after mixing a 1% solution of the product in distilled water at 37° C. for 30 minutes. For modified release products in solid dosage form (such solid dosage forms including but not limited to tablets, capsules, powders and films), release is defined as the amount of sympathomimetic amine measured using an appropriate USP dissolution test procedure with distilled water as the medium. If no official USP dissolution test procedure has been established, (e.g., as in the case of chewable tablets), then the most appropriate USP dissolution test will apply, utilizing distilled water as the medium and taking measurements at appropriate time points up to and including the final dosing interval. For modified release products in non-solid dosage form (such non-solid dosage forms including but not limited to liquids, syrups, elixers, liquid center oral products, creams, pastes and gels), release is defined as the amount of sympathomimetic amine measured after mixing a 1% solution of the product in distilled water at 37° C. for 1 hour and taking at least one additional measurement up to and including the final dosing interval.

For the purposes of this invention, the term "combination inhibitor" refers to a component of a composition which both interferes with the isolation of a sympathomimetic amine from the composition and interferes with the conversion of the sympathomimetic amine to another pharmacologically active compound. The combination inhibitor interferes with such a conversion either directly from the original formulation or after attempts have been made to isolate the sympathomimetic amine. It is both the physical and chemical properties of the combination inhibitors which allow them to act as multifaceted deterrents to the use of these compositions in the preparation of other pharmacologically active compounds. Combination inhibitors of the instant invention demonstrate all of the following characteristics: (1) they significantly interfere with chemical reactions which convert the sympathomimetic amine to another pharmacologically active compound; (2) they are not readily separable from the sympathomimetic amine to an extent that they would no longer be able to significantly interfere with chemical reactions which convert the sympathomimetic amine to another pharmacologically active compound; and, (3) they may also interfere with the separation of the sympathomimetic amine from the other components of the composition. A single combination inhibitor may be used or multiple combination inhibitors may be included in the composition of the instant invention.

In the present invention "reaction inhibitors" are components of a composition that mainly interfere with the conversion of sympathomimetic amines to other pharmacologically active compounds. Unlike combination inhibitors, under certain conditions a reaction inhibitor may be readily separable from the sympathomimetic amine to the extent that it no longer can significantly effect the chemical reactions which convert the sympathomimetic amine to another pharmacologically active compound. A single reaction inhibitor may be used or multiple reaction inhibitors may be included in the composition of the instant invention.

A "separation inhibitor" in the instant invention is a component of a composition that primarily interferes with the separation of the sympathomimetic amine from the composition. The interference with the separation is predominately due to the inability of the sympathomimetic amine to be physically isolated from the composition. Separation inhibitors are of two main types: water soluble and solvent soluble. An example of a typical separation technique which may be affected by the properties of a separation inhibitor involves the use of filtration as a means of separating the sympathomimetic amine from the composition. In the case of filtration, the separation inhibitor interferes with the filtration and results in a reduced yield of separated sympathomimetic amine. Water soluble inhibitors interfere with water based separations and solvent soluble inhibitors interfere with solvent based separations. A third class of separation inhibitors can also be used in the present invention. This class includes compounds that are soluble in both aqueous and organic solvents. A single separation inhibitor may be used or multiple separation inhibitors may be included in the composition of the instant invention.

Sympathomimetic Amines in OTC Pharmaceuticals and the Corresponding Pharmacologically Active Compounds Produced from the Sympathomimetic Amines Sympathomimetic amines are compounds that cause vasoconstriction in the vascular bed of the nasal mucosa resulting in a shrinking of the engorged mucous membranes. The ultimate physiological response is increased drainage and improved nasal air flow. As a result of these effects, sympathomimetic amines are highly effective as nasal decongestants. Unless otherwise stated, as used herein the term "sympathomimetic amine" can be used interchangeably with and may refer to a corresponding pharmaceutically acceptable acid salt form of the amine. The amine and its acid salt form may have asymmetric centers and occur as racemates, racemic mixtures, individual diastereomers, or enantiomers, with all isomeric forms being included in the present invention.

In a preferred embodiment of the present invention, the sympathomimetic amines are those with the structural formula I:

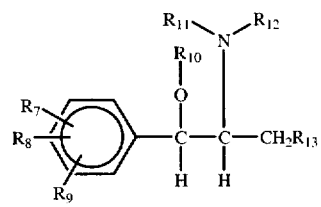

wherein $R_7$, $R_8$a $R_9$, $R_{10}$, $R_{11}$, $R_{12}$ and $R_{13}$ are selected from the following: hydrogen; substituted or unsubstituted $C_{1-12}$ alkyl; substituted or unsubstituted $C_{1-12}$ alkoxy; hydroxy; and halogen. Notwithstanding the foregoing, $R_{11}$ and $R_{12}$ are not halogens.

Those sympathomimetic amines widely available as OTC nasal decongestants are particularly contemplated for use in the instant invention; specific preferred examples include: pseudoephedrine hydrochloride, pseudoephedrine sulfate, ephedrine hydrochloride and phenylpropanolamine hydrochloride. The sympathomimetic amine phenylephrine hydrochloride is also contemplated in the instant invention. While the descriptions and examples of the compositions comprising combination inhibitors, reaction inhibitors and separation inhibitors may use a specific sympathomimetic amine such as pseudoephedrine hydrochloride, it is understood that the inhibitors are applicable to any composition comprising sympathomimetic amines and their corresponding acid salt forms.

Sympathomimetic amines in OTC preparations can be converted to a wide variety of other pharmacologically active compounds. In the instant invention the pharmacologically active compounds contemplated are ones that are used for recreational purposes in an illicit manner. Examples of such pharmacologically active compounds produced from sympathomimetic amines include, but are not limited to: methamphetamine, amphetamine, methcathinone and cathinone. The production of these illegal drugs occurs by various reductive or oxidative reactions widely known to those skilled in the art.

The Amount of Sympathomimetic Amine Relative to the Amount of Inhibitors in the Invention The ratio of sympathomimetic amine salts to the inhibitor components in any composition of the instant invention is from about 1:100 to about 100:1, preferably from about 1:10 to about 10:1. Even more preferably, the amount of sympathomimetic amine salts and inhibitor mixture in any composition of the present invention is in a ratio of about 1:5 to about 5:1.

The amount of inhibitor needed to effectively interfere with the isolation of the sympathomimetic amine and the conversion of the sympathomimetic amine to another pharmacologically active compound from a composition is dependent upon the size of the unit dose. For immediate release products, typical dosages (milligrams, mg) for commonly used sympathomimetic amine decongestants are 60 mg for pseudoephedrine hydrochloride, 10 mg for phenylephrine hydrochloride, 25 mg for phenylpropanolamine hydrochloride and 24 mg for ephedrine hydrochloride. Generally, the total quantity of the inhibitors per unit dose preparation may be varied or adjusted from about 0.1 mg to about 750 mg according to the particular application and the potency of the sympathomimetic amine salt. For example, when a 30 mg pseudoephedrine hydrochloride tablet is being prepared, the amount of the inhibitor components is in a range from about 0.3 mg to about 3000 mg, more preferably in a range from about 3 mg to about 300 mg and most preferably in a range from about 6 mg to about 150 mg. The specific amounts used in the compositions can be readily determined by one of ordinary skill in the art of pharmaceutical formulations.

The goal of the instant invention is an OTC pharmaceutical composition of a sympathomimetic amine which is not usable in illicit drug preparation. The pharmaceutical composition of the present invention comprises amounts of inhibitors sufficient to interfere with both the isolation of the sympathomimetic amine and the use of the sympathomimetic amine in chemical reactions without compromising the release, bioavailability or dosing frequency associated with the undenatured composition.

Combination Inhibitors

Combination inhibitors are components which interfere with the use of compositions of sympathomimetic amines in the production of other pharmacologically active compounds by both interfering with the isolation of the sympathomimetic amine from the composition and interfering with the conversion of the sympathomimetic amine to other pharmacologically active compounds. The presence of the combination inhibitor does not significantly alter the release of the sympathomimetic amine from the composition as compared to the undenatured composition.

In the instant invention a preferred combination inhibitor may be an amino polymer or the corresponding neutralized salt form of the amino polymer. The amino polymer, in both the amine and neutralized salt forms, has a similar solubility profile to the corresponding form of many sympathomimetic amines, making it very difficult to separate the amine from a composition containing an amino polymer. Additionally, the amino polymer inhibits the chemical conversion of sympathomimetic amines to other pharmacologically active compounds. The prior art teaches the use of unneutralized amino polymers as coating agents for sympathomimetic amines (or other pharmacologically active agents). In such references the purpose of the unneutralized amino polymer in the composition is to prevent the active ingredient (e.g., a sympathetic amine) from dissolving in the mouth and creating an undesirable taste. Thus, the unneutralized amino polymer is used in a manner specifically intended to modify the release of the coated active agent in water as compared to the uncoated active ingredient. In the instant invention the use of the unneutralized (and/or neutralized) amino polymer is specifically designed to have no significant effect on the release of the active ingredient in water as compared to the same formulation without the amino polymer.

One example of an amino polymer contemplated in this invention is a copolymer of methyl methacrylate, butyl methacrylate and dimethylaminoethyl methacrylate, also known as aminoalkyl methacrylate copolymer E, JP. A preferred copolymer of methyl methacrylate, butyl methacrylate and dimethylaminoethyl methacrylate is Eudragit-E® which is available from Rohm America, Somerset, N.J. In the instant invention the amino polymer can be from about 0% to about 100% in the neutralized salt form. In a preferred embodiment the amino polymer is from about 50% to about 100% in the neutralized salt form. More preferably, the amino polymer is from about 70% to about 100% in the neutralized salt form and most preferably it is from about 85% to about 98% in the neutralized salt form. The neutralized form of the amino polymer in the instant invention can be a salt of a strong or a weak acid. Examples of strong acids used in the preparation of a neutralized amino polymer are hydrochloric, sulfuric, nitric and phosphoric acids. Weak acids contemplated in the preparation of the neutralized amino polymer include citric, ascorbic and acetic acids. An example of a preferred form of a neutralized amino polymer is the hydrochloric acid salt form of the amino polymer. The hydrochloride salt of the amino polymer is prepared by suspending the free base in distilled water and adding hydrochloric acid. The suspension may be warmed and mixed until the solution is complete. The resultant thick, viscous solution is then dried to produce a clear, brittle film. The film is milled to produce a powder suitable for incorporation into a tablet powder blend.

In one preferred embodiment of the instant invention the amino polymer is the neutralized hydrochloride salt form of the copolymer of methyl methacrylate, butyl methacrylate and dimethylaminoethyl methacrylate. The copolymer of methyl methacrylate, butyl methacrylate and dimethylaminoethyl methacrylate can be from about 0% to about 100% in the neutralized hydrochloride salt form. In a preferred embodiment the copolymer of methyl methacrylate, butyl methacrylate, and dimethylaminoethyl methacrylate is from about 50% to about 100% in the neutralized hydrochloride salt form. More preferably, the copolymer of methyl methacrylate, butyl methacrylate and dimethylaminoethyl methacrylate is from about 70% to about 100% in the neutralized hydrochloride salt form and most preferably it is from about 85% to about 98% in the neutralized hydrochloride salt form. As an example, in an immediate release product the amino polymers and the corresponding acid salts of the amino polymers can be used in amounts (milligrams, mg) per unit dose from about 10 to about 100 mg, more preferably from about 20 to about 50 mg and even more preferably from about 30 to about 40 mg.

In one embodiment of the instant invention it is contemplated that the amino polymer is homogeneously mixed together with the sympathomimetic amine and any other components necessary to prepare the final composition. In a preferred embodiment the sympathomimetic amine is first coated with the amino polymer prior to combining these two components with any additional components required in the formulation.

In another embodiment of the instant invention, the combination inhibitor may be one or more transition metal salts. Preferably, the transition metal of the transition metal salt is chosen from the group consisting of iron, copper, zinc, cobalt, chromium, manganese and nickel. In a more preferred embodiment of the instant invention the transition metal is selected from the group consisting of iron, copper and zinc and the anion of the transition metal salt is selected from the group consisting of oxide, chloride, sulfate and gluconate. An even more preferred embodiment of the instant invention utilizes ferrous gluconate as the transition metal salt. As an example, in an immediate release product the transition metal salts can be used in amounts (milligrams, mg) per unit dose from about 0.1 mg to about 25 mg, more preferably 0.25 mg to about 15 mg and most preferably from about 0.5 mg to about 10 mg. The most preferred embodiment of a combination inhibitor in the instant invention encompasses a formulation comprising an acid salt of an amino polymer, an iron salt, a copper salt and a zinc salt. The most preferred embodiment of the instant invention comprises at least one combination inhibitor, at least one reaction inhibitor and at least one separation inhibitor.

Reaction Inhibitors

A preferred embodiment of the instant invention is a pharmaceutical composition comprising an acid salt of a sympathomimetic amine, at least one combination inhibitor and at least one reaction inhibitor. The combination inhibitor is present in amounts sufficient to interfere with both the isolation of the amine and the conversion of the amine to another pharmacologically active compound; the reaction inhibitor is present in amounts sufficient to interfere with the conversion of the amine to another pharmacologically active compound. The presence of the combination and reaction inhibitors does not significantly alter the release of the sympathomimetic amine from the composition as compared to the undenatured composition.

Reaction inhibitors useful in the instant invention include the following classes of agents of which examples of preferred compounds are listed: (1) water insoluble polyhydroxy compounds such as cellulose, ethylcellulose and microcrystalline cellulose; (2) non-polymeric (three or fewer repeating units) water soluble polyhydroxy compounds such as glycerin, sucrose, lactose, fructose, sorbitol, lactitol, maltose, other mono- and disaccharides and other sugar alcohols; and, (3) solvent soluble esters such as glycerin esters, esters of glycerin polymers, sorbitol esters, propylene glycol esters, polyethylene glycol esters, sucrose esters and esters of ethoxylated fatty acids.

The compositions according to this invention can include a single reaction inhibitor that is soluble in water, methanol, chloroform and/or other organic solvents; alternatively, the reaction inhibitor can be a mixture consisting of a group of reaction inhibitors that individually are soluble in one or more solvents but have a combined solubility profile such that they cover a range of aqueous and organic solubilities. The use of such a reaction inhibitor mixture provides a high likelihood that at least one reaction inhibitor remains with the sympathomimetic amine to interfere with subsequent chemical reactions if a separation step is successful. An example of a reaction inhibitor mixture that has combined solubility in water, methanol and chloroform could contain lactose and ethylcellulose. In one embodiment of the instant invention, at least one combination inhibitor and one reaction inhibitor are utilized.

Separation Inhibitors

One embodiment of the instant invention is a pharmaceutical composition comprising an acid salt of a sympathomimetic amine, at least one combination inhibitor and at least one separation inhibitor. In a more preferred embodiment at least one reaction inhibitor is included in the formulation. Separation inhibitors useful in the instant invention include the following classes of agents of which examples of the preferred compounds are listed: (1) water soluble celluloses such as hydroxypropyl cellulose, methylcellulose and hydroxyethycellulose; (2) polysaccharide gums such as guar and xanthan; (3) polyethylene oxide polymers such as polyethylene oxide, poly(oxypropylene)-poly(oxyethylene) block polymers and polyethylene glycols; (4) acrylic acid polymers such as carbomers; (5) starches such as pregellatinized starch, corn starch and potato starch; (6) magnesium aluminum silicates such as Veegum; (7) polyvinylpyrrolidones; and (8) clays such as Kaolin and Bentonite. As an example, in an immediate release product separation inhibitors may be used in amounts (milligrams, mg) per unit dose from about 0.1 mg to about 100 mg, more preferably from about 0.5 mg to about 75 mg and most preferably from about 1 mg to about 50 mg. The most preferred embodiment of a separation inhibitor in the instant invention comprises a separation inhibitor mixture comprising hydroxypropyl cellulose, hydroxyethylcellulose, hydroxypropyl methylcellulose, polyethylene oxide and poly(oxypropylene)-poly(oxyethylene) block polymer.

Pharmaceutical Forms of the Invention

The compositions of the instant invention may take a wide variety of forms depending upon the desired route of administration. For example, the compositions according to this invention may take the form of tablets, capsules, granules, powders, lozenges, or liquid preparations such as solutions and suspensions. Also, pharmaceutical compositions of the instant invention may be sustained release products in all the above-mentioned forms. Any combinations, compositions or products described herein are used for known indications treated by sympathomimetic amines.

The compositions of the instant invention may optionally be formulated with conventional carriers or excipients using well established techniques. Without being limited thereto, such conventional carriers or excipients include diluents, binders and adhesives (e.g., cellulose derivatives and acrylic derivatives), lubricants (e.g., magnesium stearate, calcium stearate, vegetable oils, polyethylene glycols, talc, sodium lauryl sulfate, polyoxyl ethylene monostearate), disintegrants, colorants, flavorings, preservatives, sweeteners and miscellaneous materials such as buffers and adsorbents. The compositions of the present invention in tablet form may be coated, the coating which may include one or more of the inhibitors contemplated in the instant invention. For example, Eudragit-E®, ethylcellulose, hydroxypropyl cellulose and hydroxyethyl cellulose all have been used in amounts effective to form a film coating on tablets. The purposes of these film coatings are to minimize oxidation of the tablet, prevent the user from tasting the drug, facilitate the use of high-speed packaging equipment or provide "selective release" of the active ingredient. Selective release means to prevent dissolution of the active in one part of the gastrointestinal system so that the active ingredient can be released in the desired portion of the gastrointestinal system. Also, selective release formulations may prevent release of the active ingredient in the mouth, thus masking the taste of the active ingredient. Selective release formulations are to be contrasted with "extended release" formulations which release the active over time to provide a prolonged efficacy, thereby reducing the number of dosages needed. The amount of film forming ingredient required to achieve the purposes of coating is from about 0.5% to about 10%. The film forming use of these components is distinguished from the use of these same components in the instant invention in that the amounts, purposes and tablet portion of the components are distinct. Additionally, a sugar coating on the tablet is contemplated in the instant invention. The compositions of the instant invention may be in the form of non-aqueous formulations which can be obtained by dispersing the sympathomimetic amine and inhibitors in a suitable non-aqueous based vehicle or in non-aqueous solutions such as those used in soft gelatin capsule formulations. Non-aqueous vehicles appropriate for these formulations include, for example, almond oil, arachis oil, soybean oil or fractionated vegetable oils such as fractionated coconut oil. These non-aqueous formulations may optionally include suitable viscosity enhancing agent(s) (e.g., hydrogenated edible fats, aluminum stearate) and preservative(s) (e.g., methyl, ethyl, propyl or butyl-hydroxybenzoates, sodium benzoate, or sorbic acid). Solvents used in non-aqueous solutions can include glycols, polyols and glycerin.

A large collection of additional active ingredients may optionally be present in the sympathomimetic amine and inhibitor composition of the instant invention. The suitable categories of optional active ingredients that may be employed varies widely; the individual compounds within a category may include their acid addition salts. Illustrative categories and specific examples of these optional active ingredients include but are not limited to: (a) antitussives such as dextromethorphan, dextromethorphan hydrobromide, noscapine, carbetapentane citrate, and chlophedianol hydrochloride; (b) antihistamines such as chlorpheniramine maleate, phenindamine tartrate, pyrilamine maleate, brompheniramine maleate, dexchlorpheniramine maleate, dexbromphenitamine maleate, doxylamione succinate, phenyltoloxamine citrate, diphenhydramine hydrochloride, promethazine and triprolidine hydrochloride; (c) antiasthmatic drugs such as alpha2-adrenergics (e.g., salbutamol [albuterol], terbutaline, carbuterol, broxaterol, aminophylline and theophylline; (d) analgesics such as acetaminophen; (e) non-steroidal anti-inflammatory drugs (NSAIDs) such as acetylsalicylic acid, indomethacin, acemethacin, sulindac, piroxicam, ibuprofen, naproxen, ketoprofen; and (f) expectorants such as glyceryl guaiacolate and carbocysteine.

EXAMPLES

The present invention is directed to compositions comprising an acid salt of a sympathomimetic amine and at least one combination inhibitor. The compositions may also include reaction and separation inhibitors in any mixture to assure maximum protection against the use of the sympathomimetic amine-containing compositions for illegal drug manufacture.

Compositions of the Instant Invention:

Examples A–H

The following non-limiting examples are for core tablets of pseudoephedrine-containing compositions. All of the ingredients are in mg per tablet. All of the tablets can be uncoated or coated using ingredients and processes known to those skilled in the art.

Example A

A. Combine 30 mg pseudoephedrine HCl USP/EP, 5 mg poloxamer 407 NF, 5 mg glyceryl monostearate NF, 3 mg polyethylene oxide N-60K NF, 5 mg hydroxypropyl cellulose NF and 30 mg ethylcellulose NF and mix well. This mixture is then thermally extruded to produce a granulation.
B. Add 30 mg of aminoalkyl methacrylate copolymer E, JP with 99 mg of hydrochloric acid, Normal USP. Mix these ingredients and dry.
C. Delump 2 mg of silicon dioxide NF/EP, 30 mg lactose NF, 30 mg fructose NF and 5 mg crospovidone NF.
D. Combine the material produced from step B with the granulation of step A and size through an appropriate mill.
E. Add the delumped material to the sized material and blend until uniform.
F. Sift 2.5 mg stearic acid NF and 0.5 mg magnesium stearate NF into the blend produced in step E.
G. Compress the resultant blend on a standard press to the desired weight and thickness.

Example B

A. Combine 60 mg pseudoephedrine HCl USP/EP, 10 mg poloxamer 407 NF, 10 mg glyceryl monostearate NF, 6 mg polyethylene oxide N-60K NF, 10 mg hydroxypropyl cellulose NF and 60 mg ethylcellulose NF and mix well. This mixture is then thermally extruded to produce a granulation.
B. Add 60 mg of aminoalkyl methacrylate copolymer E, JP with 100 mg of hydrochloric acid, Normal USP. Mix these ingredients and dry.
C. Delump 4 mg of silicon dioxide NF/EP, 60 mg lactose NF, 60 mg fructose NF, 4 mg ferrous sulfate USP 0.5 mg cobalt chloride, 2.5 mg crospovidone NF, 1 mg hydroxyethylcellulose NF, 1 mg hydroxypropyl methylcellulose USP, 1 mg sodium carboxymethylcellulose USP, 1 mg xanthan gum NF, 2 mg microcrystalline cellulose NF, 1 mg carrageenan NF, 1 mg guar gum NF, 1 mg sodium alginate NF, 1 mg Carbomer NF, 1 mg tragacanth gum NF, 1 mg acacia gum NF and 1 mg methylcellulose USP.
D. Combine the material produced from step B with the granulation of step A and size through an appropriate mill.
E. Add the delumped material to the sized material and blend until uniform.
F. Sift 2.5 mg stearic acid NF and 1 mg magnesium stearate NF into the blend produced in step E.
G. Compress the resultant blend on a standard press to the desired weight and thickness.

Example C

A. Combine 30 mg pseudoephedrine HCl USP/EP, 5 mg poloxamer 407 NF, 5 mg glyceryl monostearate NF, 3 mg polyethylene oxide N-60K NF, 5 mg hydroxypropyl cellulose NF and 5 mg ethylcellulose NF and mix well. This mixture is then thermally extruded to produce a granulation.
B. Add 5 mg of aminoalkyl methacrylate copolymer E, JP with 15 mg of hydrochloric acid, Normal USP. Mix these ingredients and dry.
C. Delump 2 mg of silicon dioxide NF/EP, 20 mg lactose NF, 30 mg fructose NF, 1 mg copper sulfate, 1 mg zinc gluconate, 5 mg crospovidone NF, 5 mg hydroxyethylcellulose NF and 5 mg microcrystalline cellulose NF.
D. Combine the material produced from step B with the granulation of step A and size through an appropriate mill.
E. Add the delumped material to the sized material and blend until uniform.
F. Sift 3.5 mg stearic acid NF and 0.5 mg magnesium stearate NF into the blend produced in step E.
G. Compress the resultant blend on a standard press to the desired weight and thickness.

Example D

A. Combine 30 mg pseudoephedrine HCl USP/EP, 20 mg ethylcellulose NF, 20 mg fructose USP and 5 mg crospovidone NF and mix well.
B. Dissolve 5 mg hydroxypropyl cellulose NF in water and granulate with the materials in step A. Dry this granulation.

C. Add 50 mg of aminoalkyl methacrylate copolymer E, JP with 100 mg of hydrochloric acid, Normal USP. Mix these ingredients and dry.
D. Delump 2 mg of silicon dioxide NF/EP, 1 mg chromium chloride, 0.5 mg nickelous sulfate, 5 mg poloxamer 407 NF, 3 mg polyethylene oxide N-60K NF, and 5 mg hydroxyethylcellulose NF.
E. Combine the materials produced from steps C and D and size through an appropriate mill.
F. Add the delumped material to the sized material and blend until uniform.
G. Sift 3.5 mg stearic acid NF and 0.5 mg magnesium stearate NF into the blend produced in step F.
E. Compress the resultant blend on a standard press to the desired weight and thickness.

Example E

A. Mix 20 mg ethylcellulose NF, 10 mg crospovidone NF and 30 mg fructose USP.
B. Mill 60 mg pseudoephedrine HCl USP/EP and 10 mg poloxamer 407 NF. Then mill together with the mixture from step A.
C. Add 40 mg of aminoalkyl methacrylate copolymer E, JP with 106 mg of hydrochloric acid, Normal USP. Mix these ingredients and dry.
D. Delump 4 mg of silicon dioxide NF/EP, 20 mg lactose NF, 5 mg glyceryl monostearate NF, 4 mg ferric chloride USP, 0.5 mg nickelous sulfate, 1 mg zinc sulfate, 6 mg polyethylene oxide N-60K NF, 10 mg hydroxyethylcellulose NF, 10 mg hydroxypropyl cellulose NF, 1 mg hydroxypropyl methylcellulose USP, 1 mg sodium carboxymethylcellulose USP, 1 mg xanthan gum NF, 1 mg microcrystalline cellulose NF, 1 mg carrageenan NF, 1 mg guar gum NF, 1 mg sodium alginate NF, 1 mg Carbomer NF, 1 mg tragacanth gum NF, 1 mg acacia gum NF and 1 mg methylcellulose USP.
E. Combine the materials produced from steps C and D and size through an appropriate mill.
F. Add the delumped material to the sized material and blend until uniform.
G. Sift 7 mg stearic acid NF and 1 mg magnesium stearate NF into the blend produced in step F and mix well.
H. Compress the resultant blend on a standard press to the desired weight and thickness.

Example F

A. Mix 20 mg ethylcellulose NF, 10 mg crospovidone NF and 40 mg fructose USP?
B. Mill 60 mg pseudoephedrine HCl USP/EP and 10 mg poloxamer 407 NF. Then mill together with the mixture from step A.
C. Add 40 mg of aminoalkyl methacrylate copolymer E, JP with 119 mg of hydrochloric acid, Normal USP. Mix these ingredients and dry.
D. Delump 4 mg of silicon dioxide NF/EP, 2 mg ferrous gluconate, 1 mg copper gluconate, 1 mg zinc gluconate, 6 mg polyethylene oxide N-60K NF, 10 mg hydroxyethylcellulose NF, 4 mg microcrystalline cellulose and 10 mg hydroxypropyl cellulose NF.
E. Combine the materials produced from steps C and D and size through an appropriate mill.
F. Add the delumped material to the sized material and blend until uniform.
G. Sift 7 mg stearic acid NF and 1 mg magnesium stearate NF into the blend produced in step F and mix well.
H. Compress the resultant blend on a standard press to the desired weight and thickness.

Example G

A. Mix 30 mg pseudoephedrine HCl USP/EP, 5 mg poloxamer 407 NF, 10 mg ethylcellulose NF, 20 mg fructose USP and 10 mg xanthan gum.
B. Add 20 mg of aminoalkyl methacrylate copolymer E, JP with 50 mg of hydrochloric acid, Normal USP. Mix these ingredients and dry.
C. Combine the mixtures produced in steps A and B, mix well and size through an appropriate mill.
D. Delump 2 mg of silicon dioxide NF/EP, 2 mg manganese sulfate, 2 mg zinc oxide, 3 mg polyethylene oxide N-60K NF, 5 mg hydroxyethylcellulose NF, 1 mg hydroxypropyl methylcellulose USP, 1 mg sodium carboxymethylcellulose USP, 1 mg carrageenan NF, 1 mg guar gum NF, 1 mg Carbomer NF, 1 mg acacia gum NF, 5 mg hydroxypropyl cellulose NF and 5 mg crospovidone.
E. Combine the materials produced from steps C and D and size through an appropriate mill.
F. Add the delumped material to the sized material and blend until uniform.
G. Sift 3.5 mg stearic acid NF and .5 mg magnesium stearate NF into the blend produced in step F and mix well.
H. Compress the resultant blend on a standard press to the desired weight and thickness.

Example H

A. Mix 60 mg pseudoephedrine HCl USP/EP, 10 mg poloxamer 407 NF, 15 mg ethylcellulose NF, 45 mg fructose USP and 1 mg xanthan gum.
B. Add 45 mg of aminoalkyl methacrylate copolymer E, JP with 100 mg of hydrochloric acid, Normal USP. Mix these ingredients and dry.
C. Combine the mixtures produced in steps A and B, mix well and size through an appropriate mill.
D. Delump 3 mg of silicon dioxide NF/EP, 2 mg copper sulfate, 4 mg polyethylene oxide N-60K NF, 5 mg hydroxyethylcellulose NF, 5 mg hydroxypropyl methylcellulose USP, 2 mg sodium carboxymethylcellulose USP, 2.5 glyceryl monostearate NF, 10 mg hydroxypropyl cellulose NF, 15 mg lactose NF, 3 mg ferrous sulfate USP, 7.5 mg crospovidone NF, 5 mg microcrystalline cellulose NF, 5 mg Carbomer NF and 5 mg methylcellulose USP.
E. Combine the materials produced from steps C and D and size through an appropriate mill.
F. Add the delumped material to the sized material and blend until uniform.
G. Sift 5 mg stearic acid NF and 1 mg magnesium stearate NF into the blend produced in step F and mix well.
H. Compress the resultant blend on a standard press to the desired weight and thickness.

Dissolution Tests

Several of the ingredients used in the present invention as inhibitors previously have been used in pharmaceutical compositions as controlled release agents. For example, polyethylene oxide, hydroxyethyl cellulose and hydroxypropyl cellulose have been used in tablets to provide a controlled or extended release of the active. In contrast, the present invention uses such ingredients in immediate release compositions as inhibitors of the use of the composition in the illegal production of pharmacologically active agents. Tables 1 and 2 show two examples within the scope of the present invention which release, on average, 88.5% to 91.7% of the pseudoephedrine within 45 minutes.

TABLE 1

| Vessel | 5 MIN mg/tab | % Release | 15 MIN mg/tab | % Release | 30 MIN mg/tab | % Release | 45 MIN mg/tab | % Release |
|---|---|---|---|---|---|---|---|---|
| 1 | 1.5 | 5.0 | 9.8 | 32.7 | 20.9 | 70.1 | 27.2 | 91.9 |
| 2 | 1.5 | 5.0 | 11.6 | 38.7 | 25.9 | 86.8 | 26.3 | 89.1 |
| 3 | 1.9 | 6.3 | 11.2 | 37.4 | 24.8 | 83.2 | 28.9 | 97.8 |
| 4 | 1.6 | 5.3 | 11.4 | 38.1 | 26.9 | 90.2 | 27.4 | 92.8 |
| 5 | 2.20 | 6.7 | 12.1 | 40.4 | 24.8 | 83.2 | 25.7 | 87.1 |
| 6 | 2.2 | 7.3 | 13.5 | 45.1 | 26.5 | 88.9 | 26.9 | 91.3 |
| Average | | 5.9 | | 38.7 | | 83.7 | | 91.7 |

TABLE 2

| Vessel | 5 MIN mg/tab | % Release | 15 MIN mg/tab | % Release | 30 MIN mg/tab | % Release | 45 MIN mg/tab | % Release |
|---|---|---|---|---|---|---|---|---|
| 1 | 0.0 | 0.0 | 9.5 | 31.7 | 20.0 | 67.0 | 25.0 | 84.4 |
| 2 | 0.0 | 0.0 | 7.7 | 25.7 | 15.8 | 53.0 | 25.5 | 85.9 |
| 3 | 0.0 | 0.0 | 5.6 | 18.7 | 14.4 | 48.2 | 27.1 | 91.1 |
| 4 | 0.0 | 0.0 | 8.8 | 29.3 | 20.0 | 67.0 | 25.8 | 87.1 |
| 5 | 1.6 | 5.3 | 12.4 | 41.4 | 23.0 | 77.2 | 27.3 | 92.4 |
| 6 | 0.0 | 0.0 | 10.4 | 34.7 | 22.4 | 75.1 | 26.6 | 89.9 |
| Average | | 0.9 | | 30.2 | | 64.6 | | 88.5 |

While the invention has been described in detail and with reference to specific examples thereof, it will be apparent to one skilled in the art that various changes and modifications can be made therein without departing from the spirit and scope thereof.

Extraction Tests

A formulation within the scope of the instant invention containing pseudoephedrine hydrochloride, poloxamer, aminoalkyl methacrylate copolymer E, JP, hydrochloric acid, polyethylene oxide, hydroxypropyl cellulose, ethylcellulose, hydroxyethyl cellulose, silicon dioxide, cellulose, fructose, ferrous chloride, crospovidone, stearic acid and magnesium stearate was processed and compressed into tablets. The tablets were film coated using a commercially available film coating solution containing hydroxypropyl methylcellulose.

The finished tablets were ground to a fine powder and this powder was added to a particular solvent. The pseudoephedrine hydrochloride was solubilized in the solvent and subsequently recovered by evaporation of the solvent. The resultant extract was subjected to two techniques used in the clandestine production of methamphetamine from pseudoephedrine hydrochloride. Table 3 illustrates the amount of methamphetamine recovered from the tablets following the particular extraction and conversion methodologies.

TABLE 3

| Solvent | Reaction Technique | Methamphetamine Yield (%) |
|---|---|---|
| Methanol | Hydriodic Acid + Red Phosphorous | 0.7 |
| | Lithium + Anhydrous Ammonia | <0.1 |
| Chloroform | Hydriodic Acid + Red Phosphorous | 0.2 |
| | Lithium + Anhydrous Ammonia | 0.1 |
| Hot Water | Hydriodic Acid + Red Phosphorous | 0.1 |

TABLE 3-continued

| Solvent | Reaction Technique | Methamphetamine Yield (%) |
|---|---|---|
| | Lithium + Anhydrous Ammonia | <0.1 |

What is claimed is:

1. A pharmaceutical composition comprising:
   an acid salt of a sympathomimetic amine; and
   at least one combination inhibitor, said combination inhibitor being an amino polymer or a salt of a transition metal selected from the group consisting of iron, cobalt, copper, manganese, nickel and zinc,
   wherein each said combination inhibitor is a single component and is present in amounts sufficient to interfere with the isolation of said sympathomimetic amine and to interfere with the conversion of said sympathomimetic amine to other pharmacologically active compounds without significantly altering the release of said sympathomimetic amine from said pharmaceutical composition as compared to the undenatured composition.

2. The pharmaceutical composition according to claim 1 further comprising at least one reaction inhibitor, wherein said reaction inhibitor is present in amounts sufficient to interfere with the conversion of said sympathomimetic amine to other pharmacologically active compounds without significantly altering the release of said sympathomimetic amine from said pharmaceutical composition as compared to the undenatured composition.

3. The pharmaceutical composition according to claim 1 further comprising at least one separation inhibitor, wherein said separation inhibitor is present in amounts sufficient to interfere with the isolation of said sympathomimetic amine without significantly altering the release of said sympathomimetic amine from said pharmaceutical composition as compared to the undenatured composition.

4. The pharmaceutical composition according to claim 2 further comprising at least one separation inhibitor, wherein said separation inhibitor is present in amounts sufficient to interfere with the isolation of said sympathomimetic amine without significantly altering the release of said sympathomimetic amine from said pharmaceutical composition as compared to the undenatured composition.

5. The pharmaceutical composition according to claim 1 wherein said sympathomimetic amine is selected from the group consisting of pseudoephedrine hydrochloride, pseudoephedrine sulfate, ephedrine hydrochloride and phenylpropanolamine hydrochloride.

6. The pharmaceutical composition according to claim 5 wherein said sympathomimetic amine is pseudoephedrine hydrochloride.

7. The pharmaceutical composition according to claim 1 wherein said other pharmacologically active compound is selected from the group consisting of methamphetamine, amphetamine, methacathinone and cathinone.

8. The pharmaceutical composition according to claim 7 wherein said other pharmacologically active compound is methamphetamine.

9. The pharmaceutical composition according to claim 1 wherein said amino polymer is in a neutralized salt form.

10. The pharmaceutical composition according to claim 9 wherein said amino polymer is from about 1% to about 100% in the neutralized salt form.

11. The pharmaceutical composition according to claim 9 wherein said amino polymer is from about 50% to about 100% in the neutralized salt form.

12. The pharmaceutical composition according to claim 9 wherein said amino polymer is from about 70% to about 100% in the neutralized salt form.

13. The pharmaceutical composition according to claim 9 wherein said amino polymer is from about 85% to about 98% in the neutralized salt form.

14. The pharmaceutical composition according to claim 1 wherein said amino polymer is a copolymer of methyl methacrylate, butyl methacrylate and dimethylaminoethyl methacrylate.

15. The pharmaceutical composition according to claim 14 wherein said amino polymer is the neutralized hydrochloride salt form of the copolymer of methyl methacrylate, butyl methacrylate and dimethylaminoethyl methacrylate.

16. The pharmaceutical composition according to claim 15 wherein said copolymer of methyl methacrylate, butyl methacrylate and dimethylaminoethyl methacrylate is from about 1% to about 100% in the neutralized hydrochloride salt form.

17. The pharmaceutical composition according to claim 15 wherein said copolymer of methyl methacrylate, butyl methacrylate and dimethylaminoethyl methacrylate is from about 50% to about 100% in the neutralized hydrochloride salt form.

18. The pharmaceutical composition according to claim 15 wherein said copolymer of methyl methacrylate, butyl methacrylate and dimethylaminoethyl methacrylate is from about 70% to about 100% in the neutralized hydrochloride salt form.

19. The pharmaceutical composition according to claim 15 wherein said copolymer of methyl methacrylate, butyl methacrylate and dimethylaminoethyl methacrylate is from about 85% to about 98% in the neutralized hydrochloride salt form.

20. The pharmaceutical composition according to claim 14 wherein said copolymer of methyl methacrylate, butyl methacrylate and dimethylaminoethyl methacrylate is homogeneously mixed together with said sympathomimetic asine and all other components of said pharmaceutical composition.

21. The pharmaceutical composition according to claim 14 wherein said copolymer of methyl methacrylate, butyl methacrylate and dimethylaminoethyl methacrylate coats said sympathomimetic amine prior to mixing with all other components of said pharmaceutical composition.

22. The pharmaceutical composition according to claim 1 wherein the anion of said transition metal salt is selected from the group consisting of chloride, oxide, sulfate and gluconate.

23. The pharmaceutical composition according to claim 1 wherein said transition metal salt is selected from the group consisting of ferric chloride, ferric oxide, ferrous sulfate, ferrous chloride, ferrous gluconate, ferrous oxide, zinc gluconate and copper gluconate.

24. The pharmaceutical composition according to claim 23 wherein said transition metal salt is selected from the group consisting of ferrous gluconate, zinc gluconate and copper gluconate.

25. The pharmaceutical composition according to claims 2 or 4 wherein said reaction inhibitor is selected from the group consisting of water insoluble polyhydroxy compounds, non-polymeric water soluble polyhydroxy compounds and solvent soluble ester compounds.

26. The pharmaceutical composition according to claim 25 wherein said water insoluble polyhydroxy compound is selected from the group consisting of ethylcellulose and cellulose.

27. The pharmaceutical composition according to claim 25 wherein said non-polymeric water soluble polyhydroxy compound is selected from the group consisting of fructose, glycerin, sorbitol, lactitol, mannitol, xylitol, maltitol and galactose.

28. The pharmaceutical composition according to claim 25 wherein said solvent soluble ester is selected from the group consisting of glycerin esters, esters of glycerin polymers, sorbitol esters, propylene glycol esters, polyethylene glycol esters, sucrose esters and esters of ethoxylated fatty alcohols.

29. The pharmaceutical composition according to claims 3 or 4 wherein said separation inhibitor is selected from the group consisting of water soluble cellulose compounds, polysaccharide gums, polyethylene oxide polymers, acrylic acid polymers, starches, magnesium aluminum silicates, polyvinylpyrrolidones and clays.

* * * * *

UNITED STATES PATENT AND TRADEMARK OFFICE
CERTIFICATE OF CORRECTION

PATENT NO. : 6,359,011 B1 Page 1 of 1
DATED : March 19, 2002
INVENTOR(S) : Bess et al.

It is certified that error appears in the above-identified patent and that said Letters Patent is hereby corrected as shown below:

<u>Column 18,</u>
Line 10, "asime" should read -- amine --.

Signed and Sealed this

Twenty-fourth Day of September, 2002

Attest:

JAMES E. ROGAN
*Attesting Officer*     *Director of the United States Patent and Trademark Office*